United States Patent
Ortiz Catalan et al.

(10) Patent No.: US 10,729,563 B2
(45) Date of Patent: Aug. 4, 2020

(54) ATTACHMENT DEVICE ALLOWING NATURAL WRIST ROTATION FOR OSSEOINTEGRATED PROSTHESES

(71) Applicant: Integrum AB, Mölndal (SE)

(72) Inventors: Max Jair Ortiz Catalan, Göteborg (SE); Jason Millenaar, Göteborg (SE)

(73) Assignee: Integrum AB, Mölndal (SE)

( * ) Notice: Subject to any disclaimer, the term of this patent is extended or adjusted under 35 U.S.C. 154(b) by 267 days.

(21) Appl. No.: 15/778,273

(22) PCT Filed: Nov. 28, 2016

(86) PCT No.: PCT/SE2016/051176
§ 371 (c)(1),
(2) Date: May 23, 2018

(87) PCT Pub. No.: WO2017/099648
PCT Pub. Date: Jun. 15, 2017

(65) Prior Publication Data
US 2018/0325701 A1 Nov. 15, 2018

(30) Foreign Application Priority Data
Dec. 11, 2015 (SE) ...................................... 1551627

(51) Int. Cl.
*A61F 2/58* (2006.01)
*A61F 2/78* (2006.01)
*A61F 2/54* (2006.01)

(52) U.S. Cl.
CPC ................ *A61F 2/583* (2013.01); *A61F 2/78* (2013.01); *A61F 2002/543* (2013.01); *A61F 2002/7887* (2013.01)

(58) Field of Classification Search
CPC .. A61F 2/58; A61F 2/582; A61F 2/583; A61F 2/585; A61F 2/586; A61F 2/588;
(Continued)

(56) References Cited

U.S. PATENT DOCUMENTS

| 5,443,526 A | 8/1995 | Hoerner |
| 8,795,387 B1 * | 8/2014 | Razink .................... A61F 2/585 623/62 |

(Continued)

FOREIGN PATENT DOCUMENTS

| CN | 1404803 | 3/2003 |
| DE | 102004056775 | 6/2006 |

(Continued)

OTHER PUBLICATIONS

Lisa Sellgren, PCT ISR Written Opinion, parent application # PCT/SE2016/051176, dated Feb. 17, 2017, Sweden Patent Office, Stockholm Sweden.

(Continued)

*Primary Examiner* — Suba Ganesan
*Assistant Examiner* — Aren Patel
(74) *Attorney, Agent, or Firm* — Babcock IP, PLLC (57) ABSTRACT

The present invention relates to a an attachment device for attaching a prosthesis to a bone, comprising: a base plate having an extension in an xy-plane; a first holder for holding a first abutment; a second holder for holding a second abutment; a locking plate attached to the base plate to restrict movement of the holders in a z-direction away from the base plate. The locking plate is configured to allow rotation of the first and second holder around a z-axis perpendicular to the xy-plane. The locking plate and the base plate is configured to allow movement of the first holder along the x-direction and to prevent movement the y-direction and to prevent movement of the second holder in the x- and y-direction. At least one flexible member is arranged between each of the first and second holders and the base plate, the flexible member being flexible in the z-direction to allow movement of the first and second holder in the z-direction and to allow the first and second holder to tilt with respect to the xy-plane.

17 Claims, 7 Drawing Sheets

(58) Field of Classification Search
CPC ............... A61F 2/78; A61F 2002/543; A61F 2002/7887
USPC .................................................. 623/57–65
See application file for complete search history.

(56) References Cited

U.S. PATENT DOCUMENTS

| | | | |
|---|---|---|---|
| 2003/0101838 A1* | 6/2003 | Shinozaki | A61F 2/585 74/490.05 |
| 2003/0163206 A1 | 8/2003 | Yasui et al. | |
| 2007/0021841 A1* | 1/2007 | Al-Temen | A61F 2/54 623/25 |
| 2012/0310371 A1 | 12/2012 | Bachus et al. | |
| 2015/0127114 A1* | 5/2015 | Zhao | A61F 2/58 623/22.13 |
| 2015/0025794 A1 | 9/2015 | Branemark | |
| 2016/0143751 A1* | 5/2016 | Chestek | A61F 2/583 623/25 |

FOREIGN PATENT DOCUMENTS

| | | |
|---|---|---|
| GB | 1324953 | 7/1973 |
| GB | 2488759 | 9/2012 |
| WO | 011923 | 3/2001 |

OTHER PUBLICATIONS

Hanna Harnack, EESR, counterpart EP application # EP16873457, Dec. 14, 2019, European Patent Office, Munich, DE.

\* cited by examiner

ATTACHMENT DEVICE ALLOWING NATURAL WRIST ROTATION FOR OSSEOINTEGRATED PROSTHESES

FIELD OF THE INVENTION

The present invention relates to an attachment device for a prosthetic limb. In particular, the preset invention relates to an attachment device for attaching a prosthetic device to implants in the radius bone and in the ulna bone.

BACKGROUND OF THE INVENTION

Although prosthetic limbs have been around for centuries, several problems are often experienced by amputees making use of a traditional socket attachment. These include but are not limited to: dermatological problems, and a limited range of motion. A prosthesis that does not clamp around the residual limb of the amputee but is anchored directly to the skeleton avoids socket-related problems and improves prosthesis use and quality of life substantially.

A way in which this is achieved is through osseointegration, which is described as a permanent integration between bone and a titanium implant. An extension component from the implant protrudes the skin of the patient and can be connected to the prosthesis directly, providing a skeleton-anchored attachment of the prosthetic limb. This technique is well-established in dental implants and more recently in limb amputees using systems like the OPRA (Osseointegrated Prostheses for the Rehabilitation of Amputees) Implant System.

Upper extremity amputees with an amputation below the elbow, also known as trans-radial amputation (TRA) patients, have two implants in the residual limb: one implant in the radius bone and one implant in the ulna bone. To simplify the connection of a prosthesis, an attachment device may be used as an intermediate device connecting the prosthesis to the limb, where the attachment device is connected to skeleton-anchored implants.

Due to the varying and complex anatomy of the forearm bones and due to the varying level of amputation among patients, an attachment device should be able to connect to all of these different configurations of implants and still fulfill its function. Accordingly, there is a need for an adjustable attachment device for attaching a prosthetic limb to a forearm.

SUMMARY

In view of above-mentioned desired properties of an attachment device, it is an object of the present invention to provide an attachment device which allows an adjustable and flexible connection of a prosthesis in case of a trans-radial amputation.

According to a first aspect of the invention, it is therefore provided an attachment device for attaching a prosthesis to a bone, the attachment device comprising: a base plate having an extension in an xy-plane; a first holder for holding a first abutment; a second holder for holding a second abutment, the first and second abutments being configured to be implanted in a stump; a locking plate connected to the base plate and configured to restrict movement of the holders in a z-direction away from the base plate by means of an opening in the locking element, in the xy-plane, smaller than a diameter of a lower portion of the holder, the lower portion of the holder being arranged between said base plate and said locking element in the z-direction, wherein the locking plate is further configured to allow rotation of the first and second holder around a z-axis perpendicular to the xy-plane, wherein the locking plate and the base plate is further configured to allow movement of the first holder along an x-direction of the base plate and to prevent movement of the first holder in an y-direction by means of side walls extending in the z-direction from the base plate and to prevent movement of the second holder in the x-direction and in the y-direction by means of a side wall and a dividing wall extending in the z-direction from the base plate; and at least one flexible member arranged between each of the first and second holder and the base plate, the flexible member being flexible in the z-direction and configured to allow a movement of the first and second holder in the z-direction in relation to the base plate and to allow the first and second holder to tilt with respect to the xy-plane of the base plate.

The attachment device is intended to be arranged between the abutments and the prosthesis of an upper extremity amputee having a trans-radial amputation, where one abutment is attached to the radius bone and one abutment is attached to the ulna bone through osseointegration. This means the attachment device is configured to be on one side connected to the abutments by means of the holders and on the other side connected to the prosthesis.

The base plate is defined as having an extension in an xy-plane, meaning that the xy-plane is defined as the plane of the plate which has the largest extension, and which is substantially flat. Moreover, the extension of the base plate in the z-direction, perpendicular to the xy-plane, is typically very small in relation to the extension in the x and y directions.

The locking plate is arranged to keep the holders in place and connected to the base plate which means that the movement of the holders in the z-direction is in one direction limited by the locking plate and in the other direction by the base plate. Accordingly, the locking plate prevents the holders from coming loose from the attachment device. However, the locking plate allows some holder movement in the z-direction, and also some tilting motion of the holder, as will be described below in relation to the flexible element. Moreover, the locking plate allows the holders to rotate freely around their respective z-axis. The locking plate is herein described a separate element being connected to the base plate by suitable connection means. However, the locking element may equally well be an integral part of the base plate, and made from the same piece of material as the base plate, or the locking plate may be fixedly or releasably attached to the baseplate.

The flexible member is arranged between the holders and the base plate. Thus, the movement of the holders in the z-direction and the tilting of the holders is enabled by the flexible member. Moreover, the amount of allowable movement in the z-direction can be controlled by selecting the thickness and flexibility of the flexible member. To adjust the thickness of the flexible member, the distance between the locking plate and the base plate, and/or the configuration of the holders may have to be adjusted accordingly.

When performing a rotating motion of the forearm known as the motion of pronation and supination, the two implants move with respect to each other in a complex manner. This means that when attaching a prosthetic limb to these implants, in order to preserve the ability to perform this motion an attachment mechanism must be used that allows these two implants to move with respect to each other. At the same time, this attachment must be stable and reliable. Furthermore, the exact orientation of the two implants with respect to each other differs for every patient, which means that the attachment device should be able to connect to all of these different configurations of implants and still fulfill its function.

The present invention addresses the issues related to the relative movement of the ulna bone and the radius bone, and in particular how the relative movement is handled when a prosthesis is attached to implants in a stump. Moreover, the attachment device according to various embodiments of the present invention is flexible and modular such that it easily may be adapted to the specific bone configuration of an arm of an amputee.

A further advantage of the present invention is that the attachment device allows movement of the two bones in relation to each other in all directions, i.e. movement in the xy-plane by means of the first holder being movable in an x-direction together with the individual rotation of the holder. This together with the individual tiltability and individual z translation provides a flexible and modular attachment device which can accommodate a wide range of bone configurations. Moreover, the attachment device is easy to manufacture and reliable, thereby increasing the availability while reducing the cost. Accordingly, the attachment device allows a natural wrist rotation for osseointegrated prostheses.

The base plate may comprise at least one side wall extending in the z-direction and arranged to prevent said movement of said first holder in an y-direction and to prevent movement of said second holder in said x-direction and in said y-direction. The base plate may comprise one or more continuous, semi-continuous or discrete sidewalls arranged to limit the movement of the holder in the xy-plane. In an example embodiment, the base plate may be a rectangular plate having four sidewalls at the edges of the plate and a sidewall dividing the base plate into two portions where the first holder is arranged in a first portion with sidewalls preventing movement in the x-direction while allowing movement of the holder in the y-direction in relation to the base plate. The second holder is then arranged in a second portion where movement is prevented in both the x- and y-direction. However, the second holder is still allowed to rotate, move in the z-direction and tilt.

According to one embodiment of the invention, the flexible member may be a flexible mat covering the base plate, and arranged between the holders and the base plate to allow a movement in the z-direction of the holder as well as a tilting motion and rotation. However, the flexible member may also be a gasket or the like, or a flexible mat divided into several portions for example depending on the arrangement of side walls on the base plate.

In one embodiment of the invention, the attachment device according may further comprise a slider element arranged between a portion of the first holder and the flexible member, wherein the slider element is selected from a material such that the first holder may move in the x-direction by sliding on the slider element. Depending on the choice of material and configuration of the flexible member, it may be desirable to use a slider element arranged between a contact surface of the holder and a corresponding contact surface of the flexible member to ensure that the friction is low enough to allow movement in the x-direction and rotation of the holder in relation to the base plate. If the friction between the holder and the flexible member is sufficiently low, there may not be a need for a slider element. However, in cases where the flexible member is a flexible mat made from a rubber-like material, the friction between the flexible mat and the holder may prevent the desired movement. The flexible member may also comprise a low friction surface layer or coating providing the desirable low friction between the flexible member and the contact element. Since there is a flexible member arranged also between the second holder and the base plate and to allow z-translation and tilt, it must also be ensured that the friction between the second holder and the flexible member is sufficiently low to allow rotation of the second holder, which for example may be achieved by the above described slider element. Moreover, the slider element must not be arranged to cover the entire surface of the flexible member, it is sufficient that the slider element is arranged at the portions where the holder may contact the flexible member, for all possible positions of the holders. Additionally, when using a slider element, a tilting motion of the holders, enabled by the flexible member, may cause the slider element to tilt. Alternatively, the slider element may also be somewhat flexible such that only portions of the slider element are deformed when the holder is tilted.

According to one embodiment of the invention, each of the first and second holders may be substantially cylindrical having a longitudinal axis in the z-direction, and wherein an end portion of the holder directed away from the base plate comprises a circular recess for holding the abutment. By using a cylindrical holder, rotation of the holder is easily achievable in attachment device.

According to one embodiment of the invention, the first and second holder may each comprise a first portion having a first diameter and a second portion having a second diameter, the first diameter being larger than the second diameter and wherein the first portion is arranged nearest the base plate such that the first portion engages the locking element to restrict movement of the holder in said z-direction. Thereby, the holders are connected to the base plate by means of the larger diameter portion being located between the flexible member, or the slider if one is present, and the locking element. The locking element may thus have a flange or a protruding portion located above the first portion of the holder. However, the locking element still allows the holders to rotate tilt and move a limited amount in the z-direction.

According to one embodiment of the invention, each of the first and second holders may be substantially cylindrical and having a passage through said holder in said z-direction. The passage through the holder may, in addition to receiving the abutment, allow electrodes to be connected from an end portion of the abutment, through the holder and through the base plate to a prosthetic limb, thereby making it possible to connect nerves and muscles of the arm to the prosthetic limb for controlling the limb. The base plate, flexible member and slider element would need to have corresponding opening to allow the electrodes to pass through the attachment device.

Accordingly, the base plate and the flexible member may comprise openings in locations corresponding to the passage in the first and second holder in a direction towards the base plate. The openings would furthermore correspond to all possible positions of the holders, such that the opening in the base plate, flexible member and slider element corresponding to the first holder would have an elongated shape to allow for the required movement in the x direction of the first holder.

According to one embodiment of the invention, the first and second holder may be configured to have a different height from the base plate. Since the positioning of the implants of an amputee typically differs from one person to the next, and since the relative length of the radial bone and the ulna bone may be different depending on the manner of the amputation. Accordingly, it is advantageous if the holders may be of different height to accommodate the different needs. The holders may for example have a different extension in the z-direction to provide the difference in height.

According to one embodiment of the invention, the flexible member for one of the first and second holder may be thicker than the flexible member for the other one of the first and second holder, thereby providing a way to individually vary the height of the holders. This means that the two holders may be identical, which is advantageous from a manufacturing perspective, and that only the flexible member needs to be changed to achieve different heights of the holders. The difference in thickness of the flexible member may for example be achieved by using separate flexible members for the two holders and by stacking a desired number of identical flexible members for the holder that should extend further from the base plate.

According to one embodiment of the invention, each of the first and second holder may comprise at least one opening in a sidewall of the holder to expose a base portion of an abutment arranged in the holder. Exposing a base portion of the abutment provides options for locking the abutment to the holder, which is required for attaching the prosthesis and the attachments to the abutments implanted in a stump.

Moreover, each of the first and second holders may further comprise a lock ring arranged over the at least one opening and configured to hold an abutment in place when the abutment is arranged in said holder.

According to one embodiment of the invention, the lock ring is substantially U-shaped such that it may be arranged over the holder from the side of the holder, thereby simplifying attachment and removal of the attachment device.

Furthermore, the lock ring may be flexible such that it snaps into position when arranged over said opening of said holder, thereby providing additional safety and ease of use.

According to one embodiment of the invention, the attachment device may further comprise an abutment arranged in each of the holders, wherein the abutment has a cylindrical base comprising at least one bevel, and wherein the at least one bevel is aligned with the at least one sidewall opening of said holder, and wherein the lock ring is configured to engage with the bevel to prevent the abutment from rotating in said holder and to prevent the abutment from moving in the z-direction in the holder. Through the above arrangement of the abutment, the sidewall opening in the holder and the lock ring, the abutments can be locked to the holders both in the z-direction and with respect to rotation. Since the abutments are implanted into the bones of a person, it is important that the abutments remain functional for a long period of time. If the abutments would be allowed to rotate in the holders, or move in the z-direction, the abutments might wear down more rapidly, requiring replacement. By locking the abutments to the holders such that there is no relative movement between the abutments, the holders and the lock ring, the risk of wear on the abutments is minimized. If there is wear, it would take place between the holders and the sliding elements and/or the flexible member, all of which are easily replaceable.

According to one embodiment of the invention, the attachment device may comprise at least one strain gauge arranged on at least one of the holders to detect a strain in the holder. By measuring the strain in the holder, valuable information concerning stress in the implants can be gathered. The acquired information can for example be used to determine if there is abnormal imbalance between the two abutments, or if there are stresses which indicates that the attachment device needs repair or replacement.

According to one embodiment of the invention, the attachment device may further comprise a rotation lock arrangement configured to lock a rotational position of the holders in relation to the base plate. The lock arrangement would in its locked position prevent the prosthesis from moving in relation to the arm, which for example may be desirable if the wearer want to carry heavy loads.

According to one embodiment of the invention rotation lock arrangement may comprise a rotation lock holding element arranged adjacent to the locking element, the holding element comprising a movable rotation lock engagement element configured to move between a locked position and an open position, wherein the engagement element comprises a plurality of teeth and said holders comprise recesses configured to receive the teeth such that the teeth engages the recesses to prevent the holders from rotating in relation to the base plate when the engagement element is in a locked-position.

Further features of, and advantages with, the present invention will become apparent when studying the appended claims and the following description. The skilled person realize that different features of the present invention may be combined to create embodiments other than those described in the following, without departing from the scope of the present invention.

BRIEF DESCRIPTION OF THE DRAWINGS

These and other aspects of the present invention will now be described in more detail, with reference to the appended drawings showing an example embodiment of the invention, wherein.

DETAILED DESCRIPTION OF EXAMPLE EMBODIMENTS

In the present detailed description, various embodiments of the system and method according to the present invention are mainly described with reference to an attachment device comprising a rectangular base plate. However, it should be noted that the base plate may equally well have other shapes, such as circular, elliptical etc.

Figure 1:
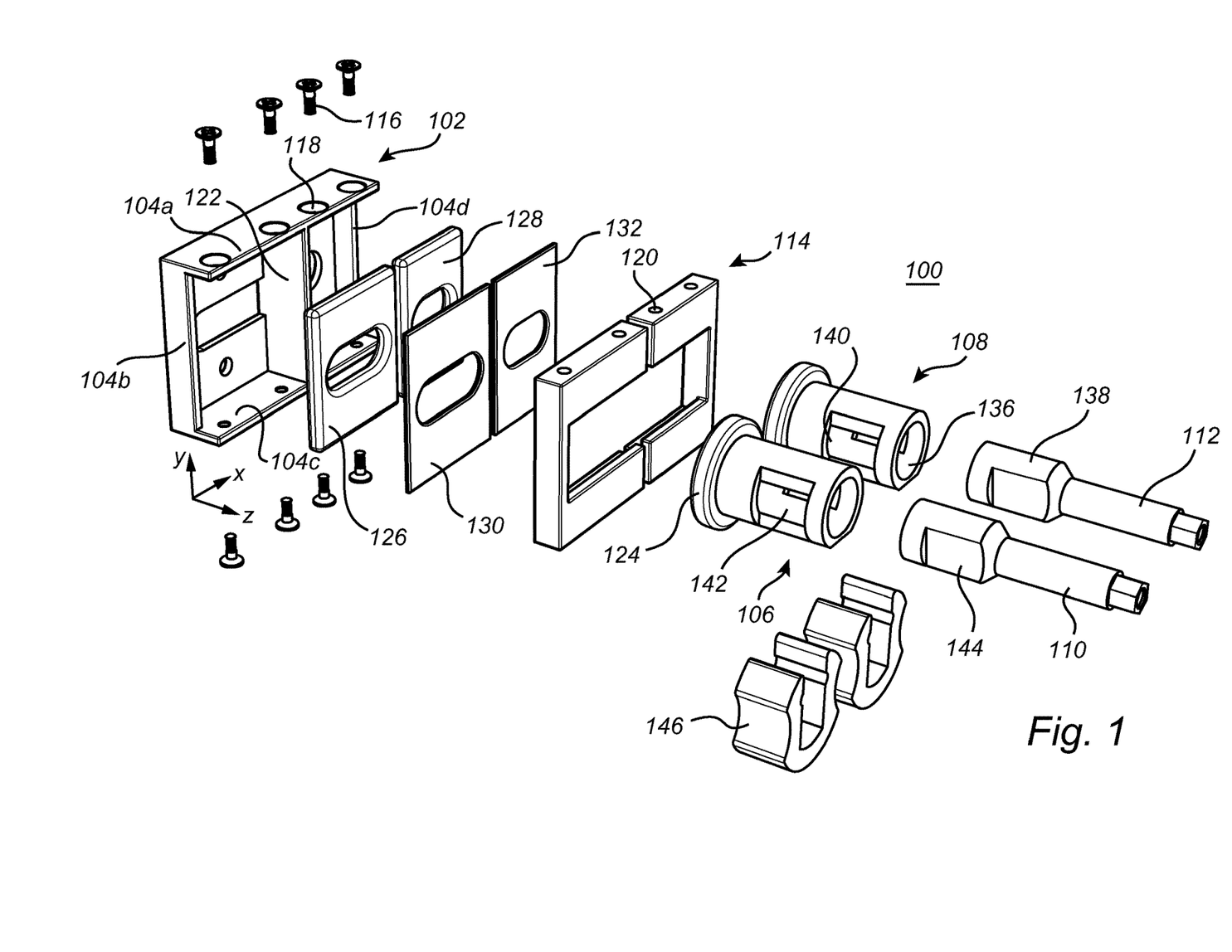
FIG. 1 schematically illustrates an attachment device according to an embodiment of the invention.

FIG. 1 schematically illustrates an attachment device 100 for attaching a prosthesis to implants in a stump. The attachment device 100 comprises a base plate 102 having an extension in an xy-plane, where the xy-plane is defined as the base plane of the base plate 102. The base plate 102 comprises four side walls 104a-d, extending in the z-direction perpendicular to the base plate 102. The attachment further comprises a first and a second holder 106, 108 for holding a corresponding first and second abutment 110, 112. In use, the abutments will be implanted into a bone of an amputee, such that the attachment device 100 acts as an intermediate element allowing a prosthesis to be attached to an arm.

The attachment device further comprises a locking element 114 which is configured to be connected to the base plate by means of screws 116 through openings 118 in the base plate and corresponding openings 120 in the locking element 114. Even though the locking element 114 is illustrated herein to consist of two separate parts, the locking element 114 may equally well be a single part or comprise a plurality of parts. A suitable locking element may also be formed as an integral part of the base plate 102.

A functional feature of the locking element 114 is that it is configured to restrict movement of the holders 106, 108 in a z-direction away from the base plate 102. In other words, the locking element 114 locks the first and second holder 106, 108 to the base plate 102, preventing them from coming off. Moreover, the locking element 114 is further configured to allow rotation of the first and second holder 106, 108 around their respective z-axis, perpendicular to the xy-plane. The locking element 114 and the base plate 102 is further configured to allow movement of the first holder 106 along the x-direction of the base plate and to prevent movement of the first holder 106 in the y-direction, and to prevent movement of the second holder 108 in both the x-direction and the y-direction. For the first holder 106, the movement in the x-direction is allowed since the distance between a side wall 104b of the base plate 102 and a dividing wall 122 is larger than a diameter of the lower portion 124 of the holder 106. The maximum, allowable movement of the first holder in the x-direction is thus limited by the side wall 104b and the dividing wall 122. In a similar manner, any movement in the xy-plane of the second holder 108 is prevented by the side walls 104a,d,c of the base plate 102 and the dividing wall 122. The skilled person readily realizes that the wall limiting the movement of the holders may be arranged and configured in many different ways. One or more of the walls may for example be part of the locking element 114 while still providing the desired functionality.

Moreover, the attachment device 102 comprises two flexible members 126, 128, arranged between each of the first and second holders 106, 108 and the base plate 102. The flexible members 126, 128 are flexible in the z-direction to allow a movement of the first and second holder 106, 108 in the z-direction in relation to the base plate 102 if the holders are exposed to a downward pressure. Accordingly, the resulting connection between a bone and a prosthesis is flexible in the z-direction by means of the attachment device 100, and the degree of flexibility can be varied by varying the thickness and elasticity of the flexible members 126, 128.

The flexible members 126, 128 also allow the holders 106, 108 to tilt with respect to the xy-plane of the base plate 102. Moreover the attachment 100 device is here illustrated to comprise first and second slider elements 130, 132 made of a material providing a low friction between the sliders 130, 132 and the corresponding holders 106, 108 allowing the holders to rotate and allowing the first holder 106 to move in the x-direction by gliding on the slider element 130. The sliding functionality may equally well be provided by single slider element for both holders 106, 108. As an alternative to slider elements, the flexible member may be from a material having a low friction to the holders, or the flexible members may have a coating or additional top layer providing the desired friction. The flexible members 126, 128 are here illustrated as flexible mats having a rectangular shape following the shape of the base plate 102. However, the flexible members may also be circular elastic gaskets or the like.

The allowable amount of tilt is in part determined by the elasticity of the flexible members 126, 128 and in part by the distance in the z-direction between the base plate 102 and the locking member 114, and can thus be varied as desired by altering either the flexible member or the locking element. Typically, it may be desirable to allow a tilt in the range of 10-20°.

The holders 106, 108 are substantially cylindrical in shape, comprising openings 134, 136 for receiving the abutments 110, 112. Moreover, the holders may be open in the bottom portion arranged nearest to the base plate 102, the opening having a diameter which is smaller than the diameter of the lower portion 138 of the abutment such that the abutments rest on the resulting ledge inside the holder. Moreover, the abutments 110, 112 may comprise passage in the z-direction through the abutments 110, 112. The opening in the abutments, 110, 112, the holders 106, 108, and the corresponding openings in the slider elements 130, 132, the flexible members 126, 128, and the base plate 102 allows electrodes to be connected from the prosthesis to nerves and muscles in the arm, thereby allowing the prosthesis to be controlled by the user.

Furthermore, each of the holders 106, 108 comprise an opening 140, 142 in the wall of the corresponding holder 106, 108. Each of the abutments, which typically are identical, has a cylindrical base comprising a bevel 144 which is to be aligned with the openings 140, 142 of the holders 106, 108 such that U-shaped locking ring 146 can be arranged over the openings 140, 142, locking the abutments 110, 112 to the holders 106, 108. The U-shaped lock ring 146 is advantageously flexible so that it snaps into place around the holder, thereby locking the abutments 110, 112 to the holders 106, 108 to prevent rotation and movement in the z-direction of the abutments 110, 112 in relation to the holders 106, 108.

Figure 2:
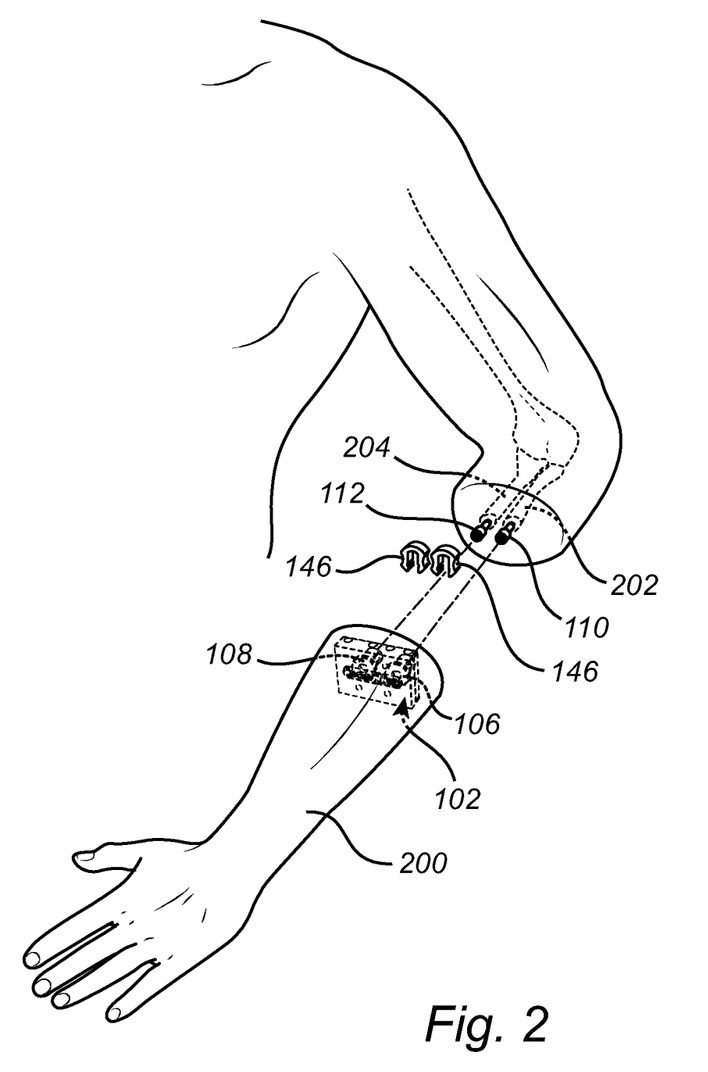
FIG. 2 schematically illustrates the use of an attachment device according to an embodiment of the invention.

FIG. 2 illustrates how the parts of an attachment device come together when attaching a prosthesis 200 to the arm of an amputee. The attachment device is fixedly connected to the prosthesis, for example by means of screws engaging corresponding openings in the bottom of the base plate 102. A first abutment 110 is implanted in the radial bone 202 and a second abutment 112 is implanted in the ulna bone 204. The attachment device is connected to the prosthesis 200 and by inserting the abutments 110, 112 into the holders 106, 108, lock rings 146 can be arranged over the holders 106, 108 to lock the prosthesis to the arm.

Figure 3A:
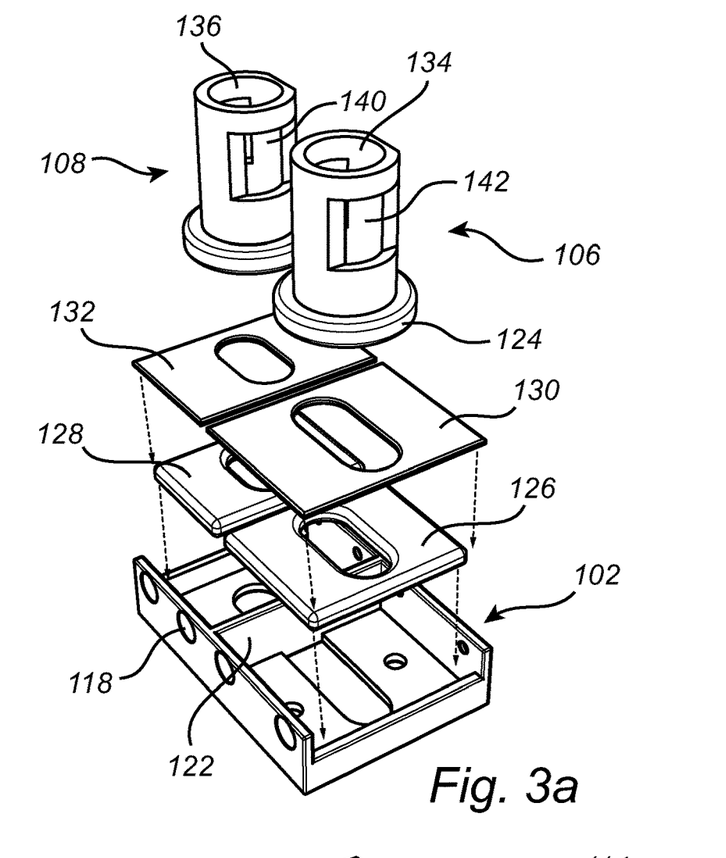
FIGS. 3a-c schematically illustrate the assembly of an attachment device according to an embodiment of the invention.
Figure 3B:
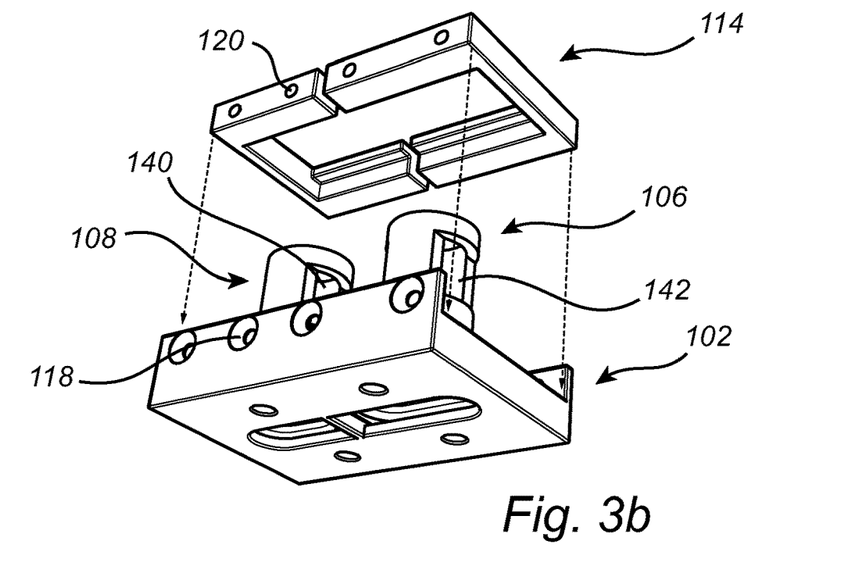
Figure 3C:
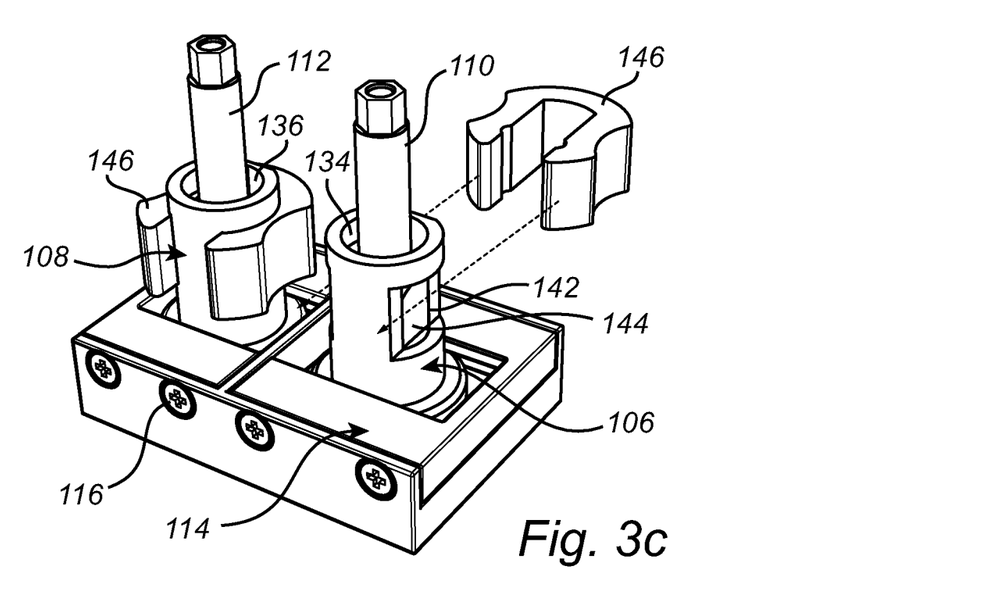

FIGS. 3*a*-*c* schematically illustrate the assembly of an attachment device 100 according to an embodiment of the invention. First, as illustrated in FIG. 3*a*, the base plate 102 is provided and flexible mats 126, 128 are arranged in the corresponding compartments of the base plate 102, where the compartments are separated by a dividing wall 122. Next, slider elements 130, 132 are arranged on top of the flexible mats 130, 132. The flexible mats 130, 132 may comprise a rubber material providing the desired elasticity and the slider elements 130, 132 may be made from a plastic material providing a sufficiently low friction to the metallic holders 106, 106 which are arranged thereon.

In FIG. 3*b* it is illustrated how the locking element 114 is arranged on top of the holders 106, 108. The locking element 114 is illustrated herein as comprising two separate pieces.

However, the locking element may equally well be a single part, comprising a cutout for accommodating the dividing wall 122.

In FIG. 3c, it can be seen how the locking element 114 is fixed to the base plate 102 by means of screws 116. Once the holders 106, 108 are locked to the base plate 102, the abutments 110, 112 may be inserted into the openings of the holders 106, 108. The bevel 144 of the abutment 110 is aligned with the sidewall opening 142 of the holder 106, so that the abutment 110 is prevented from rotating in the holder 106 when the lock ring 146 is arranged over the holder 106.

Figure 4:
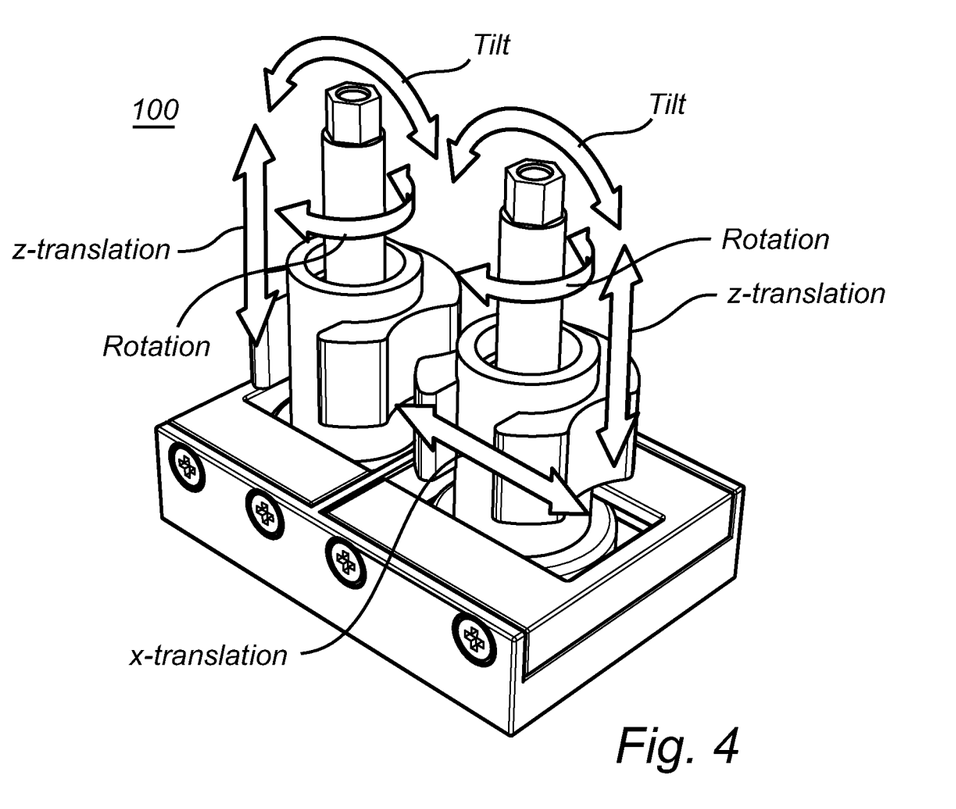
FIG. 4 schematically illustrates the functionality of an attachment device according to an embodiment of the invention.

FIG. 4 schematically illustrates the functionality of the attachment device 100 according to an embodiment of the invention. Here, it can be seen how the attachment device allows tilt, z-translation and rotation of both of the abutments, as well as x-translation of one of the abutments. This allows the radius bone and the ulna bone to move freely with respect to each other, thereby giving the user of the prosthesis the ability to perform forearm rotation.

Figure 5:
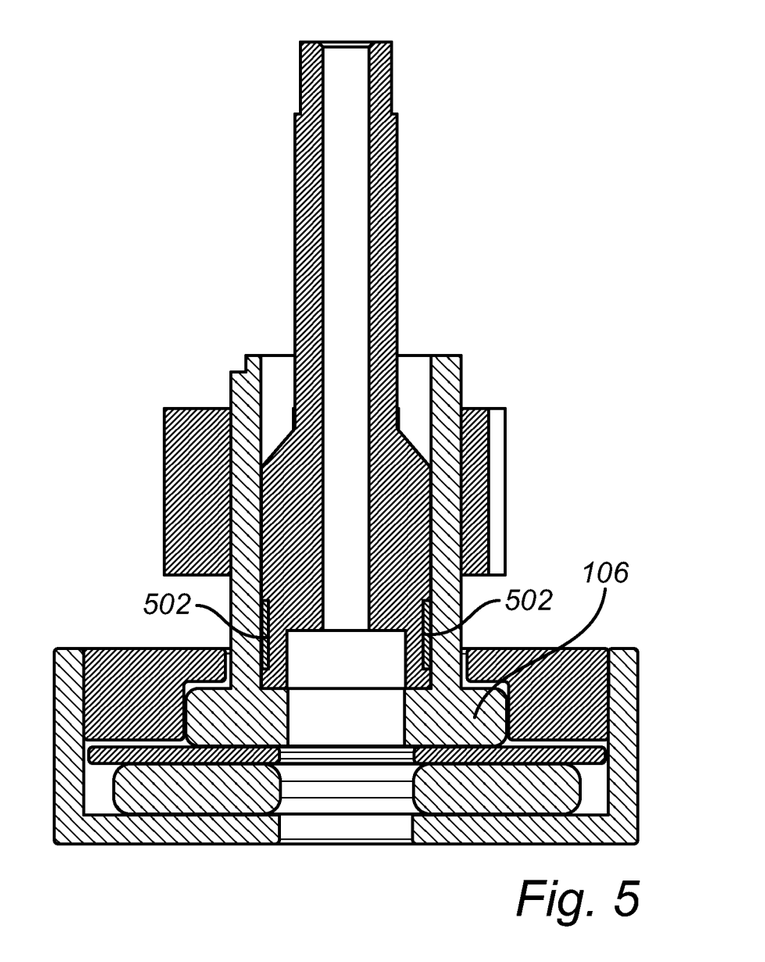
FIG. 5 schematically illustrates a portion of an attachment device according to an embodiment of the invention.

FIG. 5 schematically illustrates a portion of an attachment device according to an embodiment of the invention where a holder 106 is provided with two strain gauges 502 for measuring stress in the holder. It should be noted that each of the holders 106, 108 may comprise one or more strain gauges, for measuring stress in different orientations. The one or more strain gauges 502 may for example be arranged in a corresponding recess or channel of the holder, 106, 108, such that the holder may rotate freely. By arranging strain gauges 502 in both of the holders, it can for example be detected if one of the holders is exposed to significantly higher loads than the other.

Figure 6A:
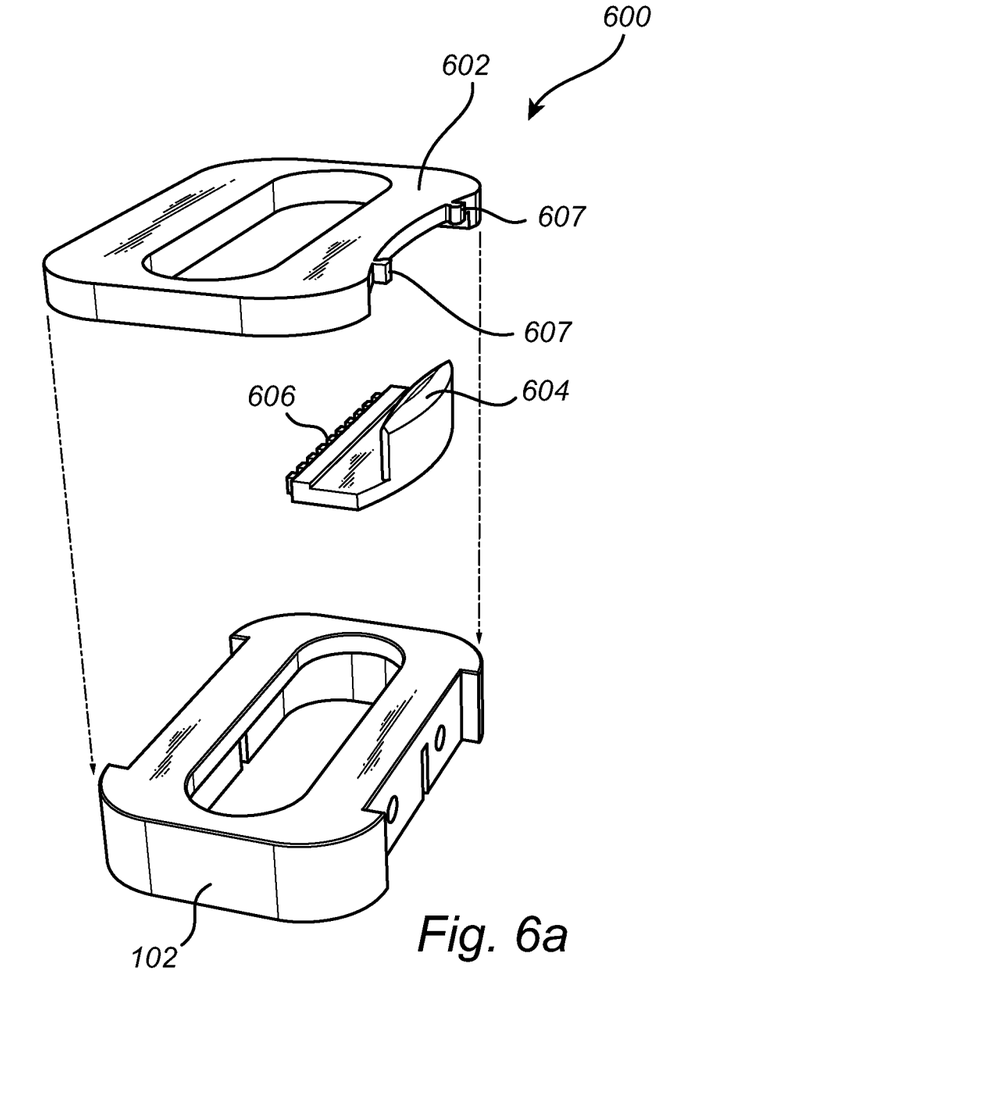
FIGS. 6A-B schematically illustrate a rotation lock arrangement and an attachment device comprising a rotation lock arrangement according to an embodiment of the invention.

FIG. 6A schematically illustrates a rotation lock arrangement 600 for an attachment device according to an embodiment of the invention. The rotation lock arrangement 600 comprises a rotation lock holding element 602 which is configured to be arranged adjacent to and on top of the locking element 114. It would also be possible to form a locking element 114 comprising an integrated rotation lock holding element 602.

The rotation lock arrangement 600 further comprises a movable rotation lock engagement element 604 configured to move between a locked-position and an open-position. The engagement element 604 comprises a plurality of teeth 606 as illustrated in FIG. 6A. When the engagement element 604 is in a locked position, it snaps into place by means of protrusions 607 having a hook shape configured to grip the sides of the engagement element 604 when moved into the locked position.

Figure 6B:
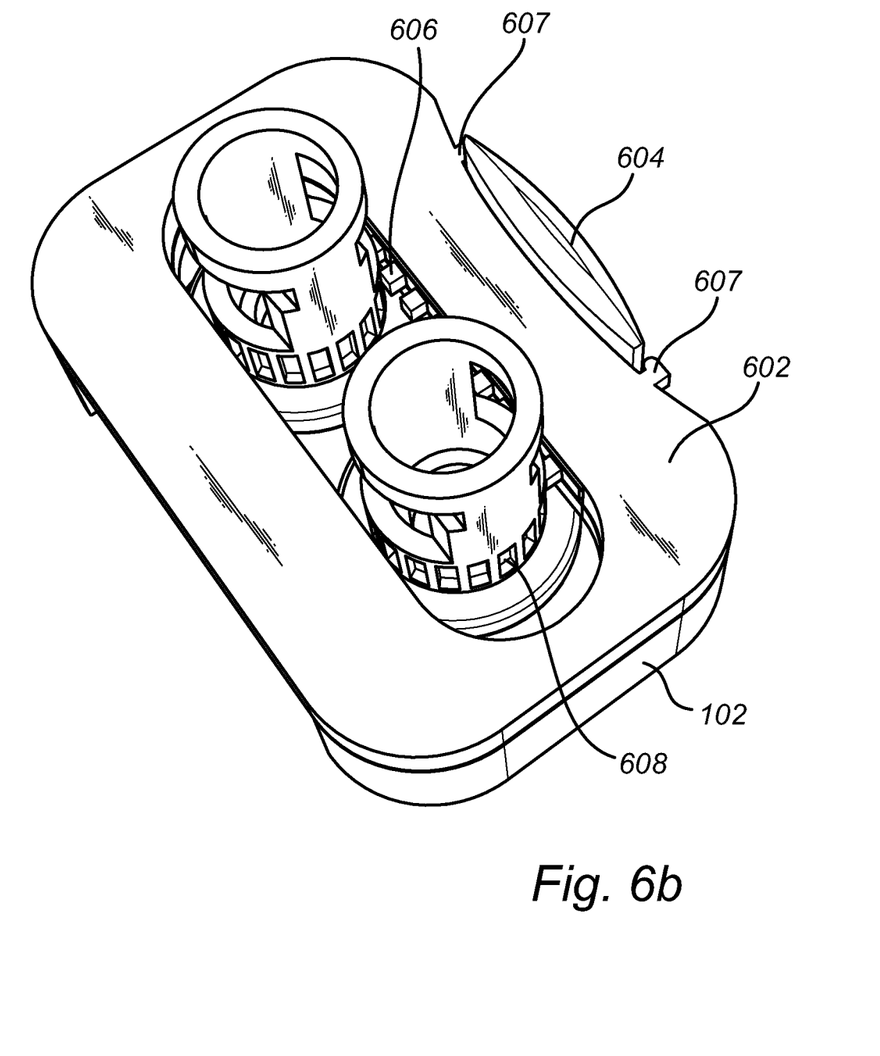

FIG. 6B illustrates an attachment device 610 comprising the rotation lock arrangement 600. Here, it can be seen that the holders comprise recesses 608 configured to receive the teeth 606 of the engagement element 604 when the engagement element is moved into the locked position such that the teeth 606 engages the recesses 608 to prevent the holders 106, 108 from rotating in relation to the base plate 102 when the engagement element 604 is in a locked-position, as illustrated by FIG. 6B.

Even though the invention has been described with reference to specific exemplifying embodiments thereof, many different alterations, modifications and the like will become apparent for those skilled in the art. As an example, the flexible members and holders may be replaced by ball joints, still allowing tilt and rotation. Moreover, the ball may be spring loaded or arranged on a separate flexible element to provide z-translation. However, a ball joint would most likely take up a larger volume than the above described configuration. Moreover, a ball joint may be more exposed to wear and tear. The attachment described above, the slider elements and flexible can easily be replaced if they are worn.

Furthermore, it should be noted that parts of the attachment device may be omitted, interchanged or arranged in various ways, the attachment device yet being able to perform the functionality of the present invention.

Additionally, variations to the disclosed embodiments can be understood and effected by the skilled person in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage.

The invention claimed is:

1. An attachment device for attaching a prosthesis to implants in a stump, said attachment device comprising:
   a base plate having an extension in an xy-plane;
   a first holder for holding a first abutment;
   a second holder for holding a second abutment, the first and second abutments being configured to be implanted in a stump;
   a locking element connected to said base plate and configured to restrict movement of said holders in a z-direction away from said base plate by means of an opening in the locking element, in the xy-plane, smaller than a diameter of a lower portion of the holders, said lower portion of the holders being arranged between said base plate and said locking element in the z-direction, wherein said locking element is further configured to allow rotation of said first and second holder around a z-axis perpendicular to said xy-plane, wherein said locking element and said base plate are further configured to allow movement of said first holder along an x-direction of said base plate and to prevent movement of said first holder in an y-direction by means of side walls extending in said z-direction from said base plate and to prevent movement of said second holder in said x-direction and in said y-direction by means of a side wall and a dividing wall extending in said z-direction from said base plate; and
   at least one flexible member arranged between each of said first and second holders and said base plate, said flexible member being flexible in said z-direction and configured to allow a movement of said first and second holder in said z-direction in relation to said base plate and to allow said first and second holder to tilt with respect to said xy-plane of said base plate.

2. The attachment device according to claim 1, wherein said flexible member is a flexible mat covering said base plate.

3. The attachment device according to claim 1, further comprising a slider element arranged between a portion of said first holder and said flexible member, wherein said slider element is selected from a material such that said first holder may move in said x-direction by sliding on said slider element.

4. The attachment device according to claim 1, wherein each of said first and second holders is substantially cylindrical having a longitudinal axis in said z-direction, and wherein an end portion of said holders directed away from said base plate comprises a circular recess for holding said abutment.

5. The attachment device according to claim 4, wherein said first and second holder each comprises a first portion having a first diameter and a second portion having a second diameter, said first diameter being larger than said second diameter and wherein said first portion is arranged nearest said base plate such that said first portion engages said locking element to restrict movement of said holder in said z-direction.

6. The attachment device according to claim 1, wherein each of said first and second holders is substantially cylindrical and having a passage through said holders in said z-direction.

7. The attachment device according to claim 6, wherein said base plate and said flexible member comprises openings in locations corresponding to the passage in said first and second holder in a direction towards said base plate.

8. The attachment device according to claim 1, wherein said first and second holder are configured to have a different height from said base plate.

9. The attachment device according to claim 8, wherein said flexible member for one of the first and second holder is thicker than the flexible member for the other one of the first and second holder.

10. The attachment device according to claim 1, wherein each of said first and second holder comprise at least one opening in a sidewall of said holders to expose a base portion of an abutment arranged in said holders.

11. The attachment device according to claim 10, wherein each of said first and second holder further comprises a lock ring arranged over said at least one opening and configured to hold an abutment in place when said abutment is arranged in said holders.

12. The attachment device according to claim 11, wherein said lock ring is substantially U-shaped.

13. The attachment device according to claim 12, wherein in said lock ring is flexible such that it snaps into position when arranged over said opening of said holders.

14. The attachment device according to claim 11, further comprising an abutment arranged in each of said holders, wherein said abutment has a cylindrical base comprising at least one bevel, and wherein said at least one bevel is aligned with said at least one sidewall opening of said holders, and wherein said lock ring is configured to engage with said bevel to prevent said abutment from rotating in said holder and to prevent said abutment from moving in said z-direction in said holders.

15. The attachment device according to claim 1, further comprising at least one strain gauge arranged on at least one of said holders to detect a strain in said holders.

16. The attachment device according to claim 1, further comprising a rotation lock arrangement (600) configured to lock a rotational position of said holders in relation to said base plate.

17. The attachment device according to claim 16, wherein said rotation lock arrangement comprises:
   a rotation lock holding element arranged adjacent to said locking element; and
   a movable rotation lock engagement element configured to move between a locked position and an open position,
   wherein said engagement element comprises a plurality of teeth and said holders comprise recesses configured to receive said teeth such that said teeth engages said recesses to prevent said holders from rotating in relation to said base plate when said engagement element is in a locked-position.

* * * * *